US005772591A

United States Patent [19]

Cram

[11] Patent Number: 5,772,591
[45] Date of Patent: Jun. 30, 1998

[54] ELECTRODE ASSEMBLY FOR SIGNALING A MONITOR

[75] Inventor: Jeffrey R. Cram, Nevada City, Calif.

[73] Assignee: Patient Comfort, Inc., Newtown, Pa.

[21] Appl. No.: 475,024

[22] Filed: Jun. 6, 1995

[51] Int. Cl.[6] .................................................. A61B 5/0492
[52] U.S. Cl. .......................... 600/383; 600/391; 600/392; 600/393; 600/546
[58] Field of Search ..................................... 128/640, 641, 128/644, 733; 607/139, 148, 149, 152; 600/383, 391, 392, 393, 546

[56] References Cited

U.S. PATENT DOCUMENTS

| 2,902,030 | 9/1959 | Kennedy et al. | 128/2.1 |
|---|---|---|---|
| 3,572,322 | 3/1971 | Wade | 128/640 |
| 3,774,593 | 11/1973 | Hakata et al. | 128/2.1 |
| 3,946,723 | 3/1976 | Servos | 128/2.1 |
| 4,082,087 | 4/1978 | Howson | 128/640 |
| 4,353,372 | 10/1982 | Ayer | 128/640 |
| 4,448,203 | 5/1984 | Williamson et al. | 128/733 |
| 4,583,549 | 4/1986 | Manoli | 128/640 |
| 4,763,660 | 8/1988 | Kroll et al. | 128/644 |

FOREIGN PATENT DOCUMENTS 2113846  8/1983  United Kingdom .

OTHER PUBLICATIONS

Ritchie, G. et al., A Microcomputer Based Controller for Neuromuscular Block During Surgery, Annals of Biomedical Engineering, 1985, 13:3–15.

Edmonds, H.L., et al., Quantitative Surface Electromyography in Anesthesia and Critical Care, Int'l. Journal of Clinical Monitoring and Computing, 1986, 3:135–145.

Chang, T., et al., Continuous Electromyography for Monitoring Depth of Anesthesia, Anesth Analg, 1988, 67:521–525.

Edmonds, H.L., et al., Objective Assessment of Opioid Action by Facial Muscle Surface Electromyography (SEMG), Prog. Neuro–Psychopharmacol. & Biol. Psychiat., 1988, 12:727–738.

Paloheimo, et al., Comparison of Neuromuscular Blockade in Upper Facial and Hypothenat Muscles, Journal of Clinical Monitoring,1988, 4:256–160.

Tammisto, T., et al., Assessment of Neuromuscular Block: Comparison of Three Clinical Methods and Evoked Electromyography, European Journal of Anaesthesiology, 1988, 5:1–8.

Nielsen, T.A., et al., Effects of Dream Reflection on Waking Affect: Awareness of Feelings, Rorschach Movement, and Facial EMG, Sleep 12, 1989, (3):277–286.

Paloheimo, M., Assessment of Anaesthetic Adequacy with Upper Facial and Abdonminal Wall EMG, European Journal of Anaesthesiology, 1988, 6:111–119.

Schwilden, H., Surveillance et Conduite de l'EEG, des Potentiels Evoques, de l'EMG du Muscle Frontal ou du Monitorage de la Contractilite Oesophagienne, Ann. Fr. Anesth. Reanim., 1989, 8:162–166.

*Primary Examiner*—Lee S. Cohen
*Attorney, Agent, or Firm*—Bernhard Kreten

[57] ABSTRACT

An electrode assembly adapted to be attached to the skin over selected facial muscle groups picks up signals to be analyzed by an anesthesia adequacy monitor that measures the level of awareness of a living animal, typically a human being. Also disclosed is a method of manufacturing the electrode assembly by printing a pattern of electrically conductive material through a silk-screen onto a flexible layer, and then coating the result with a non-conducting adhesive except at points corresponding to sensing points for the desired muscle groups. Finally, a method for using such sensing means is shown in maintaining an appropriate level of patient awareness under anesthesia.

17 Claims, 5 Drawing Sheets

PROVIDING ELECTRODE ASSEMBLY

Fig. 11

ELECTRODE ASSEMBLY FOR SIGNALING A MONITOR

FIELD OF THE INVENTION

The following invention relates to devices which are used in the field of electromyography and specifically for measuring the clinical condition of a patient under anesthesia by noting the muscular activity related to facial microexpressions. This invention is also concerned with a method for determining the adequacy of anesthesia during surgery through measuring the muscular activity of the face. This method and this device allows for quick application of multiple sensing means for the different muscles in the face.

BACKGROUND OF THE INVENTION

U.S. Pat. No. 5,195,531 describing an anesthesia adequacy monitor and method, was issued to Henry L. Bennett on Mar. 23, 1993. The disclosure of U.S. Pat. No. 5,195,531 is specifically incorporated herein by reference.

In the past, when the face was monitored for facial expressions to indicate the depth of anesthesia, individual electrodes were often applied one at a time. The time required to apply individual electrodes was significant, especially when a full surgical operating crew was standing by or there were patients waiting for their turn in the surgery operating theater.

Additionally, when individual electrodes are used, there was the problem of multiple wires leading from the patient to any type of signal receiving device. It was, of course, important to keep track of which wire was connected to which electrode and where that electrode was placed on the face or other part of the patient's body. It was also important that the wires be hooked into the proper receptacle in any type of monitor. Again, valuable time was taken up in order to assure that the wires and electrodes had been properly placed on the patient and into the monitoring device.

The following disclosures reflect the state of the art of which applicant is aware and is included herewith to discharge applicant's acknowledged duty to disclose relevant information available. It is stipulated, however, that none of these references teach singly nor render obvious when considered in any conceivable combination the nexus of the instant invention as disclosed in greater detail hereinafter and as particularly claimed.

| PATENT NO. | ISSUE DATE | INVENTOR |
| --- | --- | --- |
| 2,902,030 | September 1, 1959 | Kennedy et al. |
| 3,774,593 | November 27, 1973 | Hakata et al. |
| 3,946,723 | March 30, 1976 | Servos |
| 4,448,203 | May 15, 1984 | Williamson et al. |
| 4,583,549 | April 22, 1986 | Manoli |
| FOREIGN PATENT DOCUMENTS | | |
| GB2, 113,846 | August 10, 1983 | Rantala, B., et al. |

OTHER PRIOR ART (Including Author. Title. Date, Pertinent Pages. Etc.

Ritchie, G., et al., *A Microcomputer Based Controller for Neuromuscular Block During Surgery, Annals of Biomed. Eng.* 13:3–15 (1985)

Edmonds, H. L., et al., *Quantitative Surface Electromyography in Anesthesia and Critical Care. Int J. Clin. Monitoring and Computing* 3:135–145 (1986)

Chang, T., et al., *Continuous Electromyography for Monitoring Depth of Anesthesia, Anesth Analg.* 67:521–5 (1988)

Edmonds, H. L., et al., *Objective Assessment of Opioid Action by Facial Muscle Surface Electromyography (SEMG) Prog. Neuro-Psychopharmacol. & Biol. Psychiat.* 12:727–738 (1988)

Paloheimo, et al.: *Comparison of Upper Facial and Hypothenar Block J. of Clinical Monitoring* 4:256–260 (1988)

Tammisto, T., et al., *Assessment of Neuromuscular Block: Comparison of Three Clinical Methods and Evoked Electromyography. Eur. J. Anaesthesiol.* 5:1–8 (1988)

Nielsen, T. A., et al., *Effects of Dream Reflection on Waking Affect: Awareness of Feelings, Rorschach Movement, and Facial EMG. Sleep* 12 (3):277–286 (1989)

Paloheimo, M., *Assessment of Anaesthetic Adequacy with Upper Facial and Abdominal Wall EMG, Eur. J. Anaesthiol.* 6:111–119 (1989)

Schwilden, H., Surveillance et Conduite de l'Anesthesie a l'Aide de l'EEG. des Potentiels Evoques, de l'EMG du Muscle Frontal ou du Monitorage de la Contractilite Oesophagienne. Ann. Fr. Anesth. Reanim. 8:162–166 (1989)

McAdams, E. T., et al., *Designing Biosignal Monitoring Sensors, Sensors,* :25–27 (1994)

The Kennedy et al. patent, U.S. Pat. No. 2,902,030, described the electrodes at the bottom of column 3 as "small discs of sponge rubber wetted with saline solution or small metal disc attached to the surface of skin with adhesive tape." A good contact was provided by application of a small amount of "electrode jelly" between the skin and a metal electrode. The electrodes were applied in the supra orbital region of the head of a person. No specific facial muscle group was mentioned.

The Servos patent, U.S. Pat. No. 3,946,723, disclosed attaching a pair of electrodes to opposite temples of a patient for detecting horizontal eyeball movements using the cornea-retina potential. A second pair of electrodes attached to brow and cheek bones detected, at a different time, the cornea-retina potential showing vertical eye movement. Finally, a ground electrode was attached elsewhere on the face. The data gained was used to diagnose the presence of nystagmus as an indicator of vestibular disorders. A patient under anesthesia may not have had reliable eye movements or even any purposeful eye movements at all.

The patent Williamson, et al., U.S. Pat. No. 4,448,203 taught the use of a device for sensing electrical activity within target muscles such as the masticatory muscle. One part of the device shown was a pad with two electrodes disposed on one side and a grounding electrode disposed on the other side. The method of use for this device was for the patient to hold the electrode pad up against his face with the two electrodes sides contacting the face and the one electrode side contacting the finger of the holder. Because the patient must hold the electrode device against his face, this device was impractical for a patient under anesthesia.

The patent to Manoli, U.S. Pat. No. 4,583,549, disclosed a pad with either three or six electrodes placed in a fixed precordial configuration to assist in obtaining an ECG displaying electrical activity of the cardiac musculature. The electrodes used were either silver plated copper discs with silver/silver chloride eyelets attached to provide a convenient hook-up point for ECG recording cables, or copper discs and copper connecting paths to connector edge tab which are etched on the flexible printed circuit board (with conductive gel coated on the discs and the rest of the board coated with a non conductive adhesive and release paper). Problems remained with the manufacture of the second described electrodes because of the care necessary to assure that the conducting gel coated only the discs, that the insulating coat necessary to avoid contact between the circuits and the patient's skin was completely protective, and the necessity of hooking the six conductor cable to the connector edge tab.

The patent to Rantala taught the use of a device for measuring the depth of anesthesia which combined a surface electromyogram attached to a facial muscle with an electroencephalogram and an electromyogram attached to a patient's hand. While this application did sense the facial muscle activity, it interpreted the activity directly rather than using surface electromyogram readings to determine a facial expression corresponding to the consciousness of the patient, as does the applicant's device. Furthermore, the applicant's device uses an array of surface electromyograms providing a more accurate representation of a patient's facial expression, and hence a more accurate representation of the patient's awareness level.

The article by Ritchie, et al. in the Annals of Biomedical Engineering, 1985 described the placement of stimulating and recording electrodes on the wrist and palm of the patient. The electrodes were described as 30-gauge needles that were subcutaneously inserted near the ulnar nerve. The recording electrodes were infant EKG surface electrodes.

The article by Edmonds, et al. published in 1986 in the International Journal of Clinical Monitoring and Computing described attaching adhesive skin electrodes over the belly of the frontalis muscle and also electrodes over the temporal bone and mastoid process. This was done for the purpose of determining the level of a patient's awareness. In a later article by Edmonds, et al. in 1988 in the Prog. Neuro-Psychopharmacol. & Biol. Psychiat. an electrode was placed over the same belly of the medial frontalis muscle with a reference electrode placed over the mastoid process. Again, no more than one muscle group appears to have been attached to one individual electrode.

The article by Chang is of interest in that it also used a surface electromyogram attached to a facial muscle group and electroencephalogram data during surgery. However, the method taught in this article was designed to effectively administer anesthesia and provided no method for monitoring the awareness level of the patient for patient comfort as does the instant invention.

The article by Nielsen disclosed using electrode pairs with an interelectrode distance of 2 cm. center to center. Facial sites selected for evaluating REM sleep were right and left corrugator supercilli (for sadness brow-knitting motion) and right and left zygomaticus major (for happiness smiling). The readings were used to judge feeling-specific motor activity during imagery reflection of REM sleep, not awareness during anesthesia.

The article by Paloheimo in the 1988 *Eur. J. Anaesthiol,* told of using surface electrodes in pairs to record facial electromyographic activity. The first pair was attached on the forehead 3 cm above the mid-eyebrow and on the mastoid process, with a ground electrode on the temporal area. A second pair was located on the mamillary end anterior axillary lines 10 cm. apart within the left dermatomes, with a ground electrode on the external iliac process. No assembly of electrodes to save applying electrodes one at a time was discussed.

The second article by Paloheimo in the *J. of Clinical Monitoring* described attaching one pair of recording electrodes in the midline of the forehead and above the mid portion of an eyebrow for recording electrically evoked muscle potentials. Stimulation was provided by attaching a different pair of stimulating electrodes, one just posterior to the lower part of the pinna and the other just anterior to the tragus. The facial muscle stimulated were procerus, frontalis, corrugator, and orbicularis oculi muscles. No mention was made of recording the patient's unstimulated state.

The article by McAdams, et al. published in 1994 discussed how flexible substrates have been printed with thin layers of silver loaded ink to serve as electrodes. Also discussed was how a tab of a conductive sensor extended beyond the portion of an electrode coated with a solid, conductive adhesive hydrogel and was adapted to be connected to a monitor cable with an alligator clip. However an assembly having more than one electrode was not discussed.

The device and method of this application more effectively achieves the purpose of providing for quick and sure attachment of electrodes to the tissue of a living animal, especially the face of a human patient undergoing surgery. The electrode assembly can, when serving as the sensing means for picking up signals through the skin of facial muscle groups, provide an anesthesiologist with a reliable indicator of the patient's awareness level when the patient is otherwise uncommunicative.

SUMMARY OF THE INVENTION

The applicant's device provides an electrode assembly for monitoring differential electrical states in various parts of a living animal. In particular, the electrode assembly can be used for monitoring the nerve signals to facial muscle groups to reflect the patient's facial muscle tonus, which can be used as a reliable indicator of the level of awareness for the patient while under anesthesia. The electrode assembly, especially when it includes at least three electrodes, preferably five electrodes, can be used to monitor the difference between two muscle groups. The electrode assembly which has a pattern of electrically conductive material printed on a flexible layer, and also a non-conductive adhesive which serves to isolate electrodes from each other, is adapted to follow the facial contours of a patient. Also the electrode assembly, by having a substantially uniform thickness, prevents pressure points from developing when the electrode assembly comes between the living animal tissue and any support surface such as an operating table or bed pillow. Using the electrode assembly as a sensing means for judging the state of patient awareness, an anesthesiologist can better control and provide greater comfort for a patient undergoing anesthesia during the course of surgery. Specifically, the electrode assembly allows quick and sure attachment and a preconfigured pattern for applying the electrodes over selected facial muscle groups. The design of the electrode, with the trailing ribbon attached to the electrode sensing points in an unbroken electrical pathway, allows a monitor or other signal processing device to receive what the electrodes have picked up. After processing the signals using known algorithms, the anesthesiologist may view a display representing the patient's face derived from the processed signals. Based upon this information, the anesthesiologist then can control the dosage of anesthetic to reach the desired level of patient awareness. Additionally, the signal processor can be informed of artifact generating events which can be subtracted out from the signal received by the processor or monitor. This allows the surgeon to use such devices as an electric cauterizer during the course of surgery without interfering with the anesthesiologist efforts to maintain a desired level of patient awareness.

Fabrication of the electrode assembly can be based upon a silk-screen printing method. A flexible layer, which is characterized by resisting linear distortion, is printed with a pattern of electrically conductive material. Over this pattern is placed non-conductive adhesive either in the form of a pre-shaped pad with apertures allowing for contact with the living tissue of the animal through an electrolytic medium, or the pattern of electrically conductive material is coated with a non-conductive adhesive except at points where pads prevent coating and such points correspond to sensing points on the animal. A detachable layer over the electrode area can preserve the electrode assembly during shipping. In designing the pattern of electrically conductive materials, the locations of the Corrugator and Frontalis muscle groups can be taken into consideration for one set of electrodes, as well as the Zygomatic and Orbicularis Oculi facial muscle groups in the case of a second group of electrodes. Finally the ribbon trailing off the area of contact between the electrodes and tissue can be adapted at the opposite end to be engaged by the prongs of a spring-biased signal input clamp.

OBJECTS OF THE INVENTION

Accordingly, it is the primary object of the present invention to provide a device which allows for quick and accurate placement of electrodes upon the tissue of a living animal to monitor differential electrical states.

Another object of the present invention is to provide an electrode assembly which is easily and economically manufactured by well-known techniques such as silk-screen printing.

Another object of the present invention is to provide a sensing means preconfigured to pick up signals from certain facial muscle groups that will serve as a reliable indicator of the level of awareness of a patient undergoing anesthesia wherein the same preconfiguration arrangement of electrodes can be used with different individuals.

Yet another object of the present invention is to provide for an electrode assembly of substantially uniform thickness which assures that when the assembly is in between the patient's tissue and a bed pillow or mattress or surgery table that no pressure points are developed during the monitoring of the patient.

Another object of the present invention is to provide a method for informing an anesthesiologist of the level of patient awareness through the use of an electrode assembly which picks up signals from facial muscle groups which can be processed to provide a display representing the patient's facial muscle tonus, the display can be used by the anesthesiologist to monitor the patient's level of awareness and respond thereto with differing dosages of anesthetic.

Viewed from a first vantage point it is the object of the present invention to provide an electrode assembly for monitoring differential electrical states in various parts of a living animal, comprising: a flexible layer, a pattern of electrically conductive material, disposed upon one side of the flexible layer wherein the pattern contains at least two electrodes and is adapted to be connected to a signal receiving means, and a non-conducting adhesive that electrically isolates at least one electrode from another electrode, but allows at least two electrodes to contact the tissue of the living animal.

Viewed from a second vantage point it is the object of the present invention to provide a method for maintaining an appropriate level of patient awareness under anesthesia, the steps including: providing at least one electrode assembly, comprising a flexible layer, a pattern of electrically conductive material, disposed upon one side of the flexible layer wherein the pattern contains as at least two electrodes and is adapted to be connected to a signal receiving means, a non-conducting adhesive that electrically isolates at least one electrode from another electrode, but allows at least two electrodes to contact the tissue of said patient; and attaching the assembly to the face of the patient, picking up a signal with the electrodes, receiving the signal in a processing device through a signal receiving means, processing the signal received from the electrodes to determine what facial expression the signal represents by comparing the signals from different electrodes, the signals being reflective of the patient's facial muscle tonus, displaying the processed signal for viewing by an anesthesiologist on a display, anesthetizing the patient with an initial dosage of anesthetic to create muscle relaxation in a desired level of awareness, and controlling the patient's level of awareness.

Viewed from a third vantage point it is the object of the present invention to provide a sensing means adapted to signal an awareness level detector for informing an anesthesiologist of the level of awareness of a patient under anesthesia through detection of the patient's facial expression comprising, in combination: a flexible layer, a pattern of electrically conductive material, disposed upon one side of the flexible layer wherein the pattern contains as at least two electrodes and is adapted to be connected to a signal receiving means, a non-conducting adhesive that electrically isolates at least one electrode from another electrode, but allows at least two electrodes to contact the face of said patient.

These and other objects will be made manifest when considering the following detailed specification when taken in conjunction with the appended drawing figures.

DESCRIPTION OF PREFERRED EMBODIMENTS

Figures 1, 2:
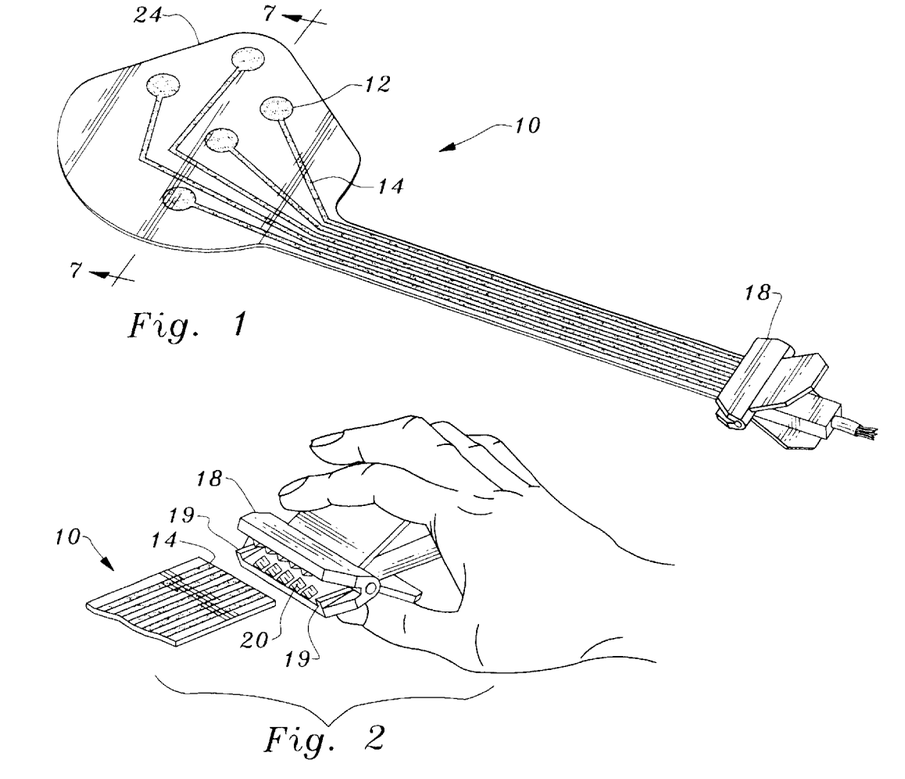
FIG. 1 is a perspective drawing of the electrode assembly as engaged with a spring biased signal receiving clamp.
FIG. 2 is a perspective drawing showing the electrode assembly being engaged by the spring biased signal receiving clamp.

Considering the drawings, wherein like reference numerals denote like parts throughout the various drawing figures, reference numeral 10 is directed to the electrode assembly according to the present invention. Referring now to FIG. 1, an electrode assembly 10 is shown engaged with spring biased signal input clamp 18. Leading from electrode contact points 12 are electrical connecting paths 14 which carry any signal received by electrode contact points 12 to spring biased signal input clamp 18. The electrode contacts points 12 and electrical connecting paths 14 are disposed upon flexible layer 24. Flexible layer 24 can be made from any of a number of flexible plastic substrates. Depending on the type of plastic used, the thickness of the flexible layer can vary from 1 mil to 3 mil, preferably being 2 mil for preferred plastic. A preferred embodiment of electrode assembly 10 uses one type of plastic that is a combination of vinyl and mylar plastics. Going on now to FIG. 2, spring bias signal input clamp 18 is shown with the jaws open ready to receive electrode assembly 10. The ribbon of the electrode is guided into the proper position in the jaws of the clamp 18 by guides 19. Contact points 20 engage individually, each one of the electrical connecting paths 14 because the electrical connecting paths 14 have been spaced apart a proper distance to ensure engagement with only one contact point 20 of spring biased signal input clamp 18. FIG. 1 does not show the electrode assembly in a perspective view of actual use, it is for illustration purposes alone. It is contemplated that the electrode assembly 10 would first be placed upon the living animal tissue, such as a patient's face, before being hooked up to spring biased signal input clamp 18. Of course, it is to be understood that other methods of engagement for electrode assembly 10 could be used to carry the signal picked up by electrode assembly 10 and deliver it to a signal processor.

Figure 3:
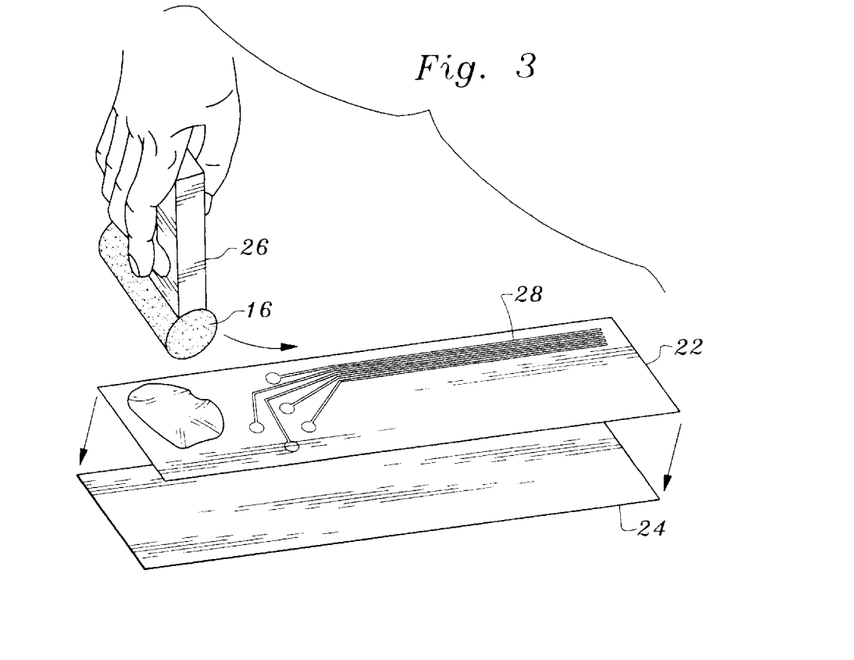
FIG. 3 is a representation of the first step fabricating the electrode assembly wherein electrically conductive material is applied to the flexible layer.

Referring now to FIG. 3, the flexible layer 24 is shown as being prepared to receive the electrically conductive material 16 that makes up electrical connecting paths 14 and electrode contact points 12. Electrically conductive material 16 is carried to mask means 22 by squeegee 26. Mask means 22 can be a silk-screen used in a silk-screen printing process. As shown, mask means 22 contains openings 28 that allows electrically conductive material 16 in squeegee 26 to flow through onto flexible layer 24 when mask means 22 is lowered into contact with flexible layer 24.

Figure 4:
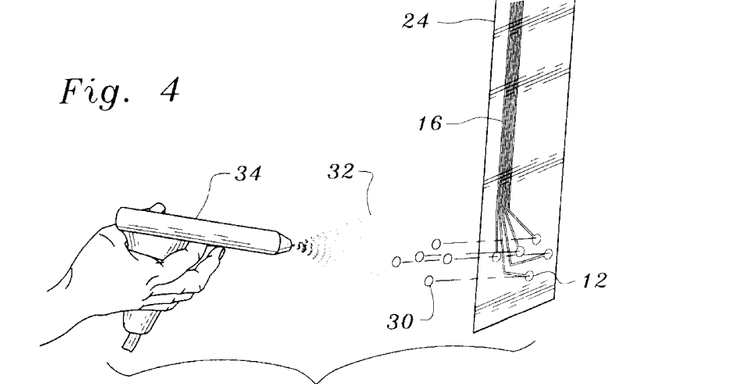
FIG. 4 is the second step in the fabrication of the electrode assembly wherein non-conductive adhesive is applied to the result of the fabrication step shown in FIG. 2.

After allowing the electrically conductive material to dry, the flexible layer 24, with a pattern of electrically conductive material 16 displayed thereon one side, can be treated in various ways to complete the fabrication of electrode assembly 10. As shown in FIG. 4, buttons 30 are placed over the electrode contact points 12. Then, non-conductive adhesive 32 is sprayed onto a side of the flexible layer 24 with the pattern of electrically conductive material 16. These buttons 30 are shown as being put into engagement with the electrode contact points 12. The electrode contact points 12 will match up with later locations on the skin of the animal. Typically the locations are placed so that the electrode contact points 12 can pick up signals from the desired muscle groups. Non-conductive material 32 is now applied by spray gun 34 to coat the entire surface of flexible layer 24 including electrically conductive material 16 and buttons 30. After the material has been sprayed on, the buttons 30 do not adhere to the electrode contact points 12. This allows easy removal of any non-conductive material from the area over the electrode contact points 12, especially if a non-conductive material 32 has been scored over the perimeter of electrode contact points 12.

Other methods of applying non-conductive material 32 can include a second silk-screen printing similar to FIG. 3. Also the non-conductive material 32 might be applied using a printing roller without any mask means, as long as buttons 30 are used. However the non-conductive material 32 is applied to flexible layer 24, it is necessary to ensure that the electrically connecting paths 14 and electrode contact points 12 do not come into contact with each other. If allowed to, this could well short out the pathway for delivering the signal received to the processor unit.

Figure 5:
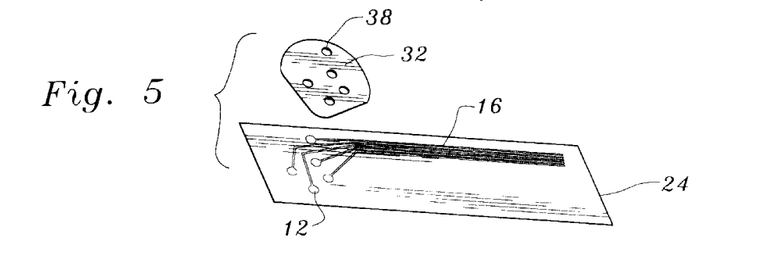
FIG. 5 is a perspective view of an alternate second step wherein a preformed shape of non-conductive adhesive is about to be mated with the result of the fabrication step shown in FIG. 2.

Another way to apply the non-conductive material 32 to flexible layer 24 with electrically conductive material disposed on one side is for a pre-formed shape, like a pad, 32 to be placed over the flexible layer 24 with electrically conductive material 16 on one side as shown in FIG. 5. Within this pre-formed layer, at the appropriate spots over the electrode contact points 12, are apertures 38, preferably filled with an electrolytic medium 40 seen later in FIG. 7 such as lanolin based cream containing electrolytes (such as Singa Creme 1705 available from Parker Laboratories). When applied to the tissue of a living animal, the apertures allow signals to be received by electrode contact points 12, especially if an electrolytic medium is used. Because the layer is pre-formed, mating it with the pattern of electrode contact points 12 on flexible layer 24 should not require much micro-adjustment of the location.

Figure 6:
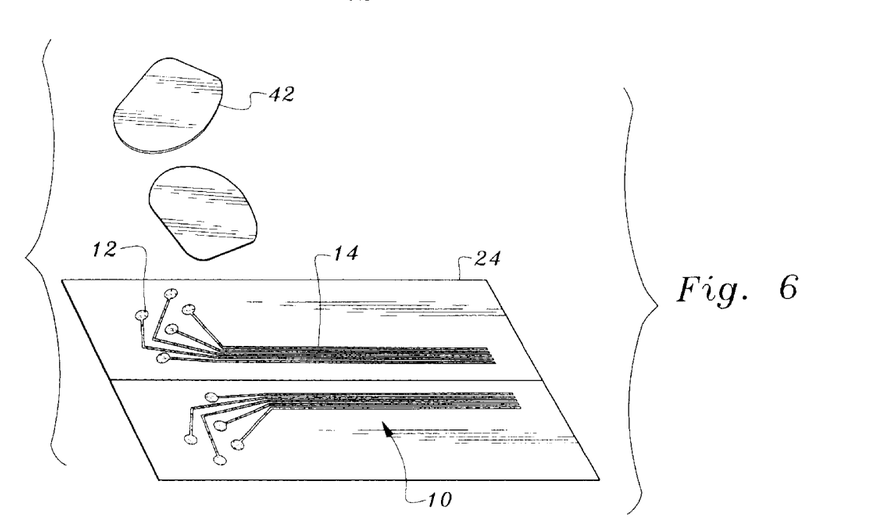
FIG. 6 is a perspective view of the third step in the fabrication process wherein a detachable pad is applied to the result of the second step of the fabrication process.

Referring now to FIG. 6, flexible layer 24 with electrical connecting paths 14 and electrode contact points 12 and non-conductive material 32 applied is ready for mating with detachable pads 42. As can also be seen in FIG. 6, electrode assemblies 10 are often produced in multiple numbers on a single flexible sheet 24. After detachable pads 42 are mated with the electrode assemblies 10, the assemblies 10 can be separated. Separation can be done through use of a knife, scissors, or other appropriate cutting means. As can be observed in FIG. 6, the electrode assemblies are sometimes mirror images of each other. Also, depending upon the muscle groups that the user may wish to monitor, electrode assemblies 10 can assume different configurations for their electrode contact points. Although FIGS. 3, 4 and 5 show only the preparation of a single electrode assembly, the silk-screen mask 22 can have many electrode assembly patterns present and a number of electrode assemblies 10 can be printed onto a flexible layer 24.

Figure 7:
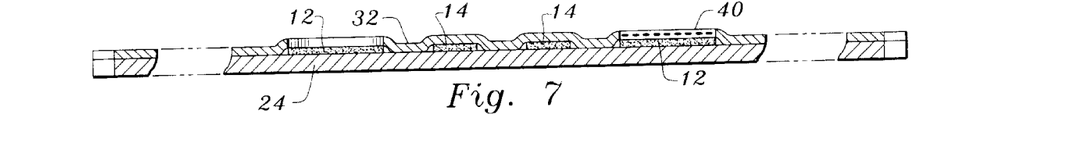
FIG. 7 is a cross section view of the electrode assembly taken along line 7—7 of FIG. 1.

Referring now to FIG. 7, the electrode assembly 10 is seen in cross section. Flexible layer 24 accounts for much of the thickness of the assembly 10. Differing electrical connecting paths 14 and the electrode contact points 12 are also present. The space above contact points 12 is vacant, while non-conductive adhesive 32 is above other parts of flexible layer 24. At the far right, the space above contact point 12 is pre-filled with electrolytic medium 40. However, the substantially uniform thickness of electrode assembly 10 is preserved due to the thinness of the non-conductive adhesive 32. Thus, the presence or absence of non-conductive adhesive 32 does not radically change the thickness of electrode assembly 10. Therefore, when electrode assembly 10 is between the tissue of a living animal and a support means, such as an operating table or a pillow on a bed, then substantially uniform thickness prevents any point from becoming a pressure point. The lack of pressure points in electrode assembly 10 when so used prevents the development of sores and other discomfort for the patient.

Figure 8:
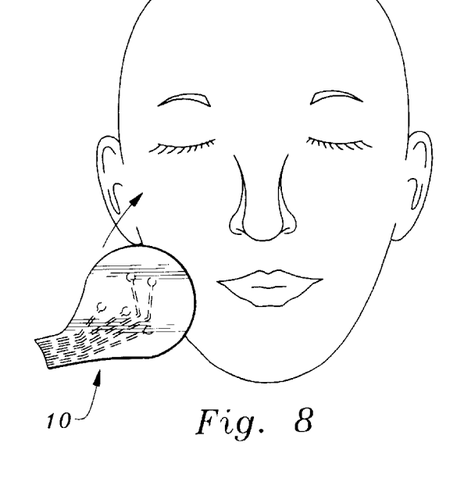
FIG. 8 is a perspective view of the electrode assembly being applied to the person's face after application of an electrolytic medium to the electrode contact points.

Referring now to FIG. 8, a patient's face is prepared to receive electrode assembly 10 which has no electrolytic medium packaged with it. An electrolytic medium 40 such as Signa brand creme, can be applied to the electrode assembly, if the assembly is not provided with a medium already in contact wells over control points 12. This medium 40 comes in the form of a thick lotion. The medium is preferably thick enough to hold a bead shape in the well of the electrode contact point. Other electrode assemblies 10 can be supplied with the medium in the well, before the detachable pads 42 are mated to the flexible layer 24. Other electrolytic mediums 40 such as electrode paste with adhesive characteristics can be applied to the electrode assembly 10. The skin over the orbicularis oculi 48 muscle group and the zygomatic 50 muscle groups in FIG. 8 is shown as ready to receive the electrode assembly 10. FIG. 8 also shows electrode assembly 10 being positioned to be applied to the patient's face over the muscle groups whose monitoring is desired. In a similar fashion, other muscle groups can have electrolytic medium 40 put into the contact points wells, and then electrode assemblies 10 applied.

Figure 9:
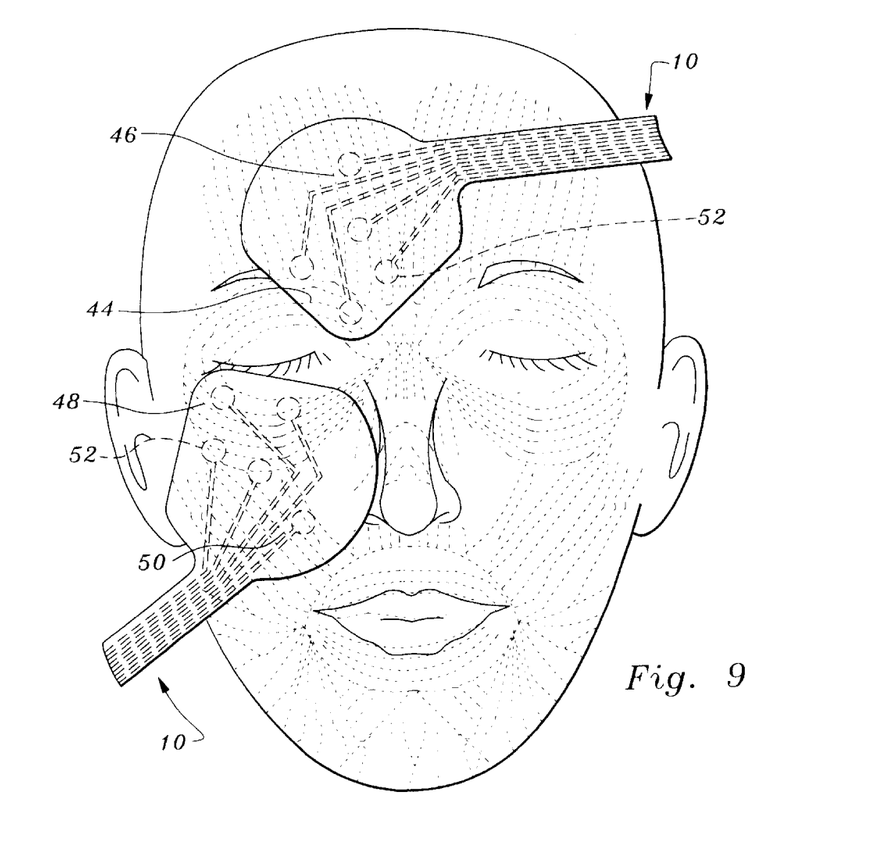
FIG. 9 is a front plan view of two devices of this application in place on a person's face.

Now referring to FIG. 9, electrode assemblies 10 have been applied to different areas of a human face. The uppermost assembly 10 is applied to the corrugator 44 facial muscle group and the frontalis 46 facial muscle group. For the lower electrode assembly, the orbicularis oculi 48 facial muscle group is contacted by the upper half of the electrode. The lower inner electrode contact points are over the zygomatic facial muscle group 50. Ground electrodes 52 are also present in each electrode assembly 10 shown in FIG. 9.

After applying the electrode assembly 10 with the electrolytic medium 40 in the electrode contact point wells, the heat of the patient's skin causes some mediums, such as the aforementioned Signa creme to partially liquify and flow into the patient's sweat glands. This flow establishes better electrical contact and hence the electrode assembly 10 can better pick up the nerve impulses to the target muscle groups. If the electrolytic medium 40 does not liquify, sometimes the patient's sweat glands produce perspiration which establishes a better electrical pick-up of nerve signals.

Figure 10:
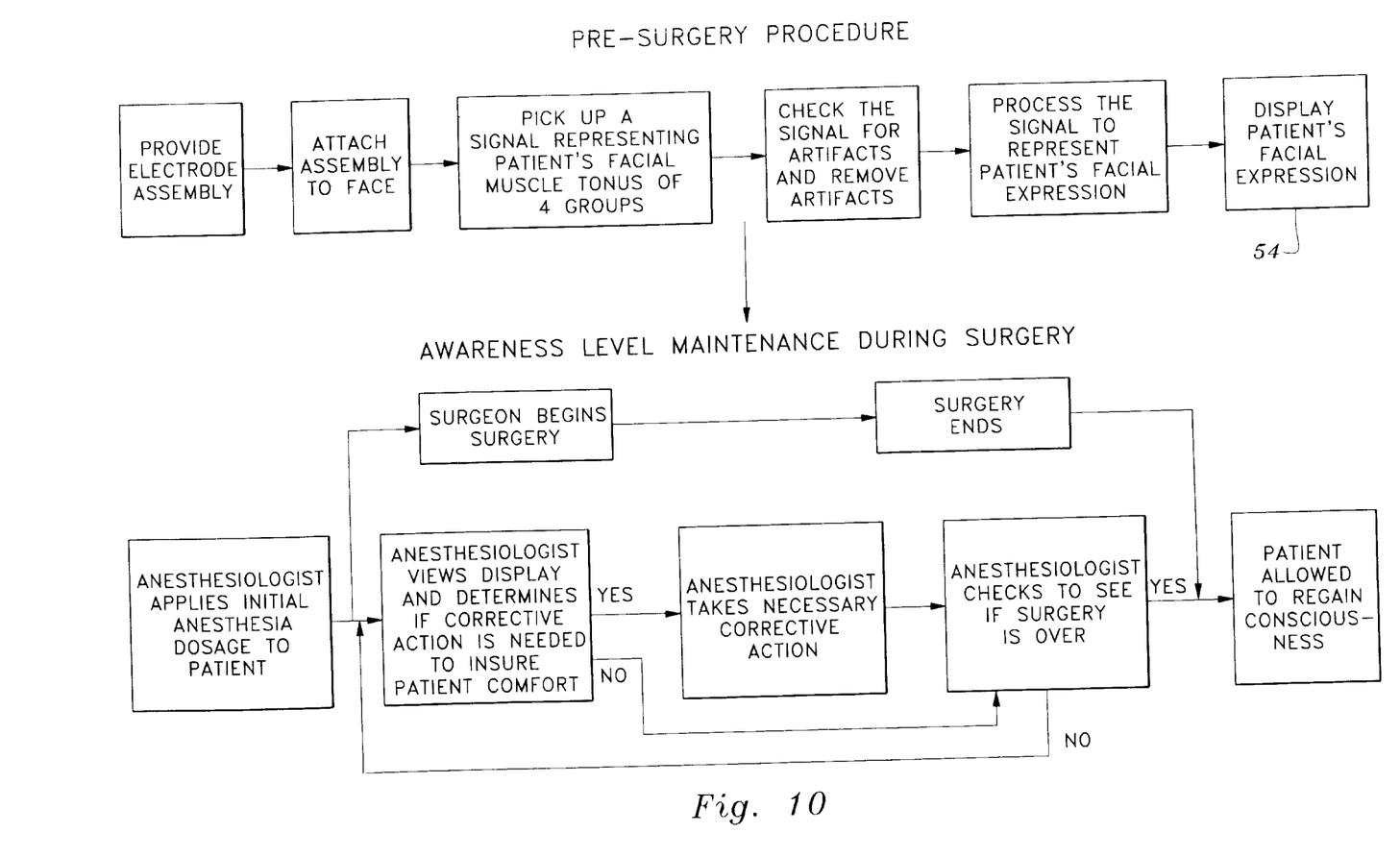
FIG. 10 is a block diagram representing the relationships of the steps of the method of this application.

Referring now to FIG. 10, in use and operation the awareness level monitor receives signals from electrode assembly 10 placed upon the face of the patient. The monitor may be used by an anesthesiologist or other qualified operator to maintain the appropriate level of patient awareness during surgery. Initially, the anesthesiologist confirms the electrode assembly proper placement on the face of the patient. Base line reading may be then established. The patient is then given anesthesia appropriate for the circumstances. The anesthesiologist may then monitor the display 54 to determine the patient's level of awareness as reflected in changes in the muscle tonus. Once surgery begins, the anesthesiologist may use the display 54 to monitor the magnitude of the patient's response to what otherwise would be an objectively painful surgical stimulus. If the display 54 demonstrates an unacceptably high level of awareness, the anesthesiologist may administer more anesthesia or take other corrective action. If the display 54 demonstrates an unacceptably low level of awareness, other corrective measures may be taken. In this way the patient's comfort may be maximized and the patient's reaction to the surgical procedure and therefore recovery time can be minimized.

Also necessary to have a accurate display 54 is the removal of artifacts in the signal caused by such artifact generators as electric cauterizing devices. When this device is used, some electric current flows through the patient causing an anomaly in the signals as read by the electrode contact points 12. The artifact detector connected on one end to the cauterizing device or other artifact generator and on the other end to a first signal conduit. When an artifact is detected by the artifact detector, the detector then filters out the portion of the first signal representing the artifact.

Figure 11:
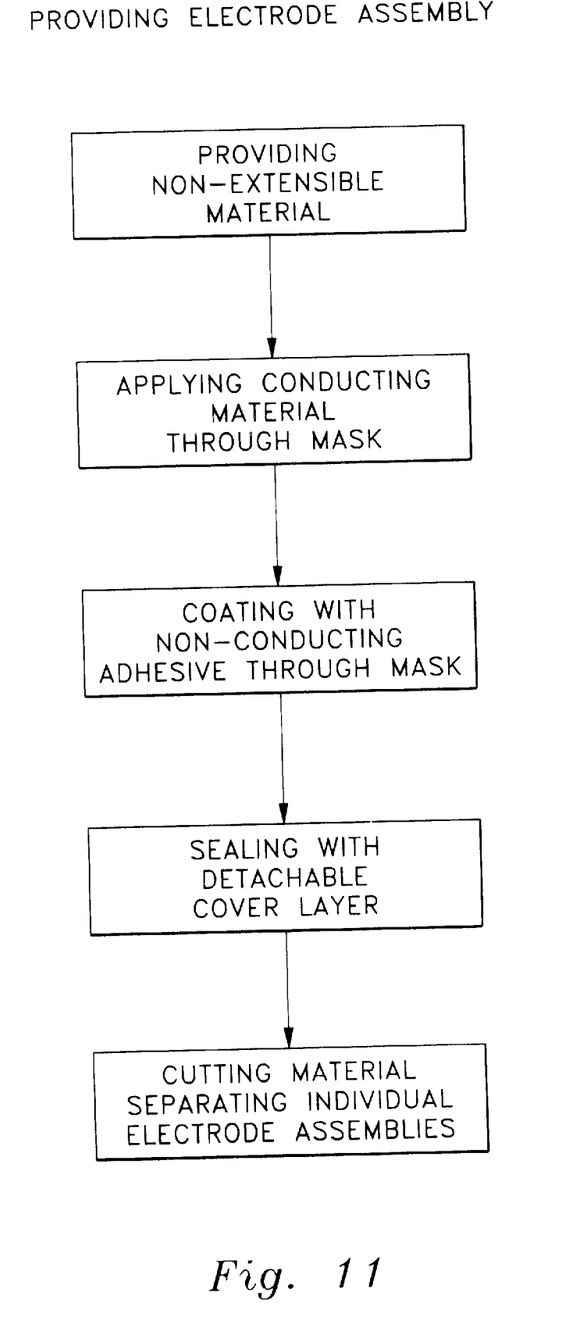
FIG. 11 is a block diagram representing the fabrication steps involved in manufacturing the device of this application.

Referring now to FIG. 11, a block diagram showing the manufacturing method for providing an electrode assembly is displayed. The first step, as previously shown in FIGS. 3, 4, 5, and 6, is to provide a non-extensible material to serve as flexible layer 24. The next step is to apply electrically conductive material 16 through mask means 22 to flexible layer 24. After this is accomplished, the next step is to coat with a non-conducting adhesive 32, preferably through a mask means. As has been previously discussed this is one method. Other methods may include mating a pre-formed layer including the flexible layer 24 with an attached pattern of electrically connecting paths 14. The next step is for a detachable pad 42 to be engaged with the now non-conducting adhesive coated flexible layer. Finally, if there are more than one electrode assemblies 10 on the flexible layer 24, the material must be cut so that the individual assemblies 10 can be separated.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An electrode assembly for an awareness level monitor, comprising, in combination:

a flexible layer a plurality of electrodes oriented in fixed positions and integrally formed with said flexible layer, said electrode assembly further including plural electrical connecting paths disposed on said flexible layer extending from said plural electrodes which are also located on said flexible layer to an input of the awareness level monitor, with each said electrode having its own said path, said electrodes located in clusters of fixed arrays to measure facial muscle tonus as artifacts of patient awareness, one cluster including one said array oriented to measure the tonus of the corrugator facial muscle group and another said array to measure the tonus of the frontalis facial muscle group.

2. The assembly of claim 1 including another cluster on said flexible layer and also coupled to said input of the awareness level monitor with one said array oriented to measure the tonus of the orbicularis oculi facial muscle group and another said array to measure muscle tonus of the zygomatic facial muscle group.

3. The assembly of claim 2 wherein said clusters are located on separate electrode assemblies, one assembly the mirror image of the other assembly and wherein the combination of assemblies is coupled to said input of the awareness level monitor.

4. The assembly of claim 3 including a ground electrode for each cluster also located on said flexible layer and having an electrical connecting path disposed thereon.

5. The assembly of claim 4 including means for removing anomalous surgically induced artifact generators coupled between said electrical connecting paths and said input of the awareness level monitor.

6. The assembly of 5 wherein said layer is linearly non-extensible along said electrical paths to thwart breaks in conductivity along said paths.

7. The assembly of claim 6 including an adhesive coating on said layer overlying said electrical paths, but free from said electrodes.

8. The assembly of claim 7 including a conductive coating overlying said electrodes.

9. The assembly of claim 8 including a removeable protective layer overlying said adhesive and conductive coating.

10. An electrode assembly for an awareness level monitor, comprising, in combination:
- a flexible layer,
- a plurality of electrodes oriented in fixed positions and integrally formed with said flexible layer,
- said electrode assembly further including plural electrical connecting paths disposed on said flexible layer extending from said plural electrodes which are also located on said flexible layer to an input of the awareness level monitor, with each said electrode having its own said path,
- said electrodes located in clusters of fixed arrays to measure facial muscle tonus as artifacts of patient awareness,
- one cluster including one said array oriented to measure the tonus of the orbicularis oculi facial muscle group and another said array to measure muscle tonus of the zygomatic facial muscle group.

11. The assembly of claim 10 including another cluster on said flexible layer and also coupled to said input of the awareness level monitor with one said array oriented to measure the tonus of the corrugator facial muscle group and another said array to measure the tonus of the frontalis facial muscle group.

12. The assembly of claim 11 wherein said clusters are located on separate electrode assemblies, one assembly the mirror image of the other assembly and wherein the combination of assemblies is coupled to said input of the awareness level monitor.

13. The assembly of claim 12 including a ground electrode for each cluster also located on said flexible layer and having an electrical connecting path disposed thereon.

14. The assembly of claim 13 including means for removing anomalous surgically induced artifact generators coupled between said electrical connecting paths and said input of the awareness level monitor.

15. The assembly of 14 wherein said layer is linearly non-extensible along said electrical paths to thwart breaks in conductivity along said paths.

16. The assembly of claim 15 including an adhesive coating on said layer overlying said electrical paths, but free from said electrodes.

17. The assembly of claim 16 including a conductive coating overlying said electrodes.

\* \* \* \* \*